(12) United States Patent
Silver

(10) Patent No.: US 12,137,993 B1
(45) Date of Patent: *Nov. 12, 2024

(54) ADVANCED SYSTEM AND METHOD FOR A DEEP TISSUE MASSAGER

(71) Applicant: Alan H. Silver, Coral Springs, FL (US)

(72) Inventor: Alan H. Silver, Coral Springs, FL (US)

( * ) Notice: Subject to any disclaimer, the term of this patent is extended or adjusted under 35 U.S.C. 154(b) by 380 days.

This patent is subject to a terminal disclaimer.

(21) Appl. No.: 17/466,004

(22) Filed: Sep. 3, 2021

Related U.S. Application Data

(63) Continuation of application No. 16/041,202, filed on Jul. 20, 2018, now Pat. No. 11,109,918, which is a continuation of application No. 14/215,377, filed on Mar. 17, 2014, now Pat. No. 10,034,813.

(60) Provisional application No. 61/801,133, filed on Mar. 15, 2013.

(51) Int. Cl.
*A61B 34/30* (2016.01)
*A61H 7/00* (2006.01)

(52) U.S. Cl.
CPC ............. *A61B 34/30* (2016.02); *A61H 7/001* (2013.01); *A61H 7/007* (2013.01); *A61H 2201/0153* (2013.01); *A61H 2201/0176* (2013.01); *A61H 2201/1215* (2013.01); *A61H 2201/1481* (2013.01); *A61H 2201/1671* (2013.01); *A61H 2201/5061* (2013.01); *A61H 2201/5082* (2013.01)

(58) Field of Classification Search
CPC ...... A61H 7/00–002; A61H 7/004–005; A61H 23/00–02; A61H 23/0254–0263; A61H 2023/0281; A61H 39/007; A61H 2201/12–1223; A61H 2201/1671
See application file for complete search history.

(56) References Cited

U.S. PATENT DOCUMENTS

| | | | |
|---|---|---|---|
| 3,252,775 | A | 5/1966 | Tocci-Guilbert |
| 4,098,266 | A | 7/1978 | Muchisky et al. |
| 4,102,334 | A | 7/1978 | Muchisky |
| 4,175,548 | A | 11/1979 | Henry |
| 4,495,940 | A | 1/1985 | Takaishi |
| 5,083,552 | A | 1/1992 | Lipowitz |
| 5,437,607 | A | 8/1995 | Taylor |
| 5,940,888 | A | 8/1999 | Sher |
| 6,648,904 | B2 | 11/2003 | Altshuler |
| 6,758,826 | B2 | 7/2004 | Luettgen et al. |
| 9,446,260 | B2 | 9/2016 | Jagger |
| 2004/0077978 | A1 | 4/2004 | Nelson et al. |
| 2005/0148910 | A1 | 7/2005 | Skover et al. |
| 2007/0123808 | A1 | 5/2007 | Rhoades |
| 2007/0219474 | A1 | 9/2007 | Wen et al. |
| 2007/0282228 | A1 | 12/2007 | Einav et al. |
| 2008/0267447 | A1 | 10/2008 | Kelusky |
| 2009/0204061 | A1 | 8/2009 | Pomposelli et al. |
| 2009/0222024 | A1 | 9/2009 | Naldoni |

(Continued)

OTHER PUBLICATIONS

USPOT Office Action dated Nov. 24, 2020, U.S. Pat. No. 16,041,202, Filing Date: Jul. 20, 2018.

*Primary Examiner* — Rachel T Sippel
(74) *Attorney, Agent, or Firm* — Jose Gutman; Fleit Intellectual Property Law

(57) ABSTRACT

A system, device, and method for therapeutic deep tissue massage is disclosed. The therapeutic deep tissue massage device includes an apparatus for use in therapeutic massage applications in which forces are provided to an outer surface of a user's body, whether human or animal, and subcutaneously within the user's tissues.

20 Claims, 5 Drawing Sheets

(56) References Cited

U.S. PATENT DOCUMENTS

| | | |
|---|---|---|
| 2011/0055720 A1 | 3/2011 | Potter et al. |
| 2011/0118641 A1 | 5/2011 | Gomez |
| 2012/0071794 A1 | 3/2012 | Karni |
| 2013/0131562 A1 | 5/2013 | Wu |
| 2013/0325182 A1 | 12/2013 | Setrakian et al. |
| 2014/0052707 A1 | 2/2014 | Jindra |
| 2014/0142478 A1 | 5/2014 | Malaviya |

ADVANCED SYSTEM AND METHOD FOR A DEEP TISSUE MASSAGER

CROSS-REFERENCE TO RELATED APPLICATIONS

Background

The present disclosure generally relates to deep tissue massagers, and more particularly relates to an apparatus for use in therapeutic massage applications in which forces are provided to an outer surface of the human body and subcutaneously within human tissues.

Traditional massage therapy has not changed significantly since its inception in 2330BC. Frequently the daily demands placed on many humans today produces pain in the neck, shoulders, lower backs, legs and more. These pains are a result of overworked muscles that never fully return to a relaxed state, but instead are overworked repeatedly until they are contracted so as to better protect the muscle tissues to from being strained or torn. These repeated patterns of overuse frequently lead to a constant state of contraction or chronic muscle spasm.

Traditional massage therapy only relieves these problems for short periods of time, and is ineffective on deep muscle spasms unless numerous massages are scheduled over a period of days, weeks or months. Human Skin is comprised of a.) the epidermis, b.) the dermis, and c.) the hypodermis. More recent massage techniques employ the means to promote circulation within the blood and lymphatic vessels present in the skin, but are largely ineffective in doing so.

In order for professional massage, sports or physical therapists to be most effective, they must be very physically fit, as to provide an effective deep tissue massage requires exerting great forces for long periods of time. Additionally, professionals must provide a series of deep tissue massages in succession, which requires even greater physical stamina, that frequently result in repetitive stress or other injuries to the professional.

In using conventional devices and methods for deep tissue massage, it has been found inconvenient, for example, that in an effort to penetrate severe muscle spasms, even professional therapists can inflict pain, or cause bruising to the skin in an effort to penetrate a severe or deep muscle spasm. Motorized massage devices typically have had a contact surface arrangement including a composition of rigid plastic or terry cloth in direct contact with a patient's skin which during operation of the device can result in chafing, abrasion, or bruising of the massaged skin or tissue. Additionally, the terry cloth or a similar pad cover can be prone to disintegrate into airborne particles, which when breathed in, causes respiratory complications to the sinuses, throats and lungs in both the therapist and the patient.

BRIEF SUMMARY

According to an embodiment of the present disclosure, a motorized therapeutic massage device is disclosed. The device includes an electrical motor having a motor drive shaft, disposed within an enclosure; and a contact surface arrangement coupled to said motor drive shaft, by means of a transfer member disposed within an enclosure, that is offset from the center axis of the motor drive shaft and a center axis of the contact surface arrangement; and wherein the motor and driveshaft are coupled to drive the contact surface arrangement to impart both random orbital oscillating motion and percussive motion to the contact surface arrangement; and further wherein the contact surface arrangement creates a penetrating shockwave subcutaneously through human or animal muscle tissue, and minimizes the frictional engagement of skin or garments covering the skin, and minimizes temperature increase of the contact surface arrangement and the skin resulting from the frictional engagement.

In an embodiment of the present disclosure, a method of applying mechanical oscillating energy through human or animal muscle tissue comprises: contacting an area of skin covering human or animal muscle tissue, with a contact surface arrangement of a mechanical oscillation treatment device and applying power to a motor of said device while said contact surface arrangement is in contact with the area of human or animal tissue to apply random orbital oscillating energy to the tissue by oscillating the contact surface arrangement in a direction approximately parallel to a surface of the tissue in a random orbital motion having a variable orbit diameter to induce shearing and stretching forces in the tissue.

In an embodiment of the present disclosure, a method of applying mechanical oscillating energy through human or animal muscle tissue comprises: contacting an area of skin covered human or animal muscle tissue, with a contact surface arrangement of a mechanical oscillation treatment device and applying power to a motor of said device while said contact surface arrangement is in contact with the area of human or animal tissue to apply orbital oscillating energy to the tissue by oscillating the contact surface arrangement in a direction approximately perpendicular to a surface of the tissue in a random orbital motion having a variable orbit diameter to induce shearing and stretching forces in the tissue.

In an embodiment of the present disclosure, a method of applying mechanical oscillating energy through human or animal muscle tissue comprises: contacting an area of skin covered human or animal muscle tissue having muscle tension or soreness, with a contact surface arrangement of a mechanical oscillation treatment device and applying power to a motor of said device while said contact surface arrangement is in contact with the area of human or animal tissue to apply orbital oscillating energy to the tissue by oscillating the contact surface arrangement in a direction having both parallel and perpendicular components to a surface of the tissue in a random orbital motion to induce shearing and stretching forces in the tissue.

BRIEF DESCRIPTION OF THE DRAWINGS

The accompanying figures, in which like reference numerals refer to identical or functionally similar elements throughout the separate views, and which together with the detailed description below are incorporated in and form part of the specification, serve to further illustrate various embodiments and to explain various principles and advantages all in accordance with the present disclosure, in which.

DETAILED DESCRIPTION

Introduction

Figure 1:
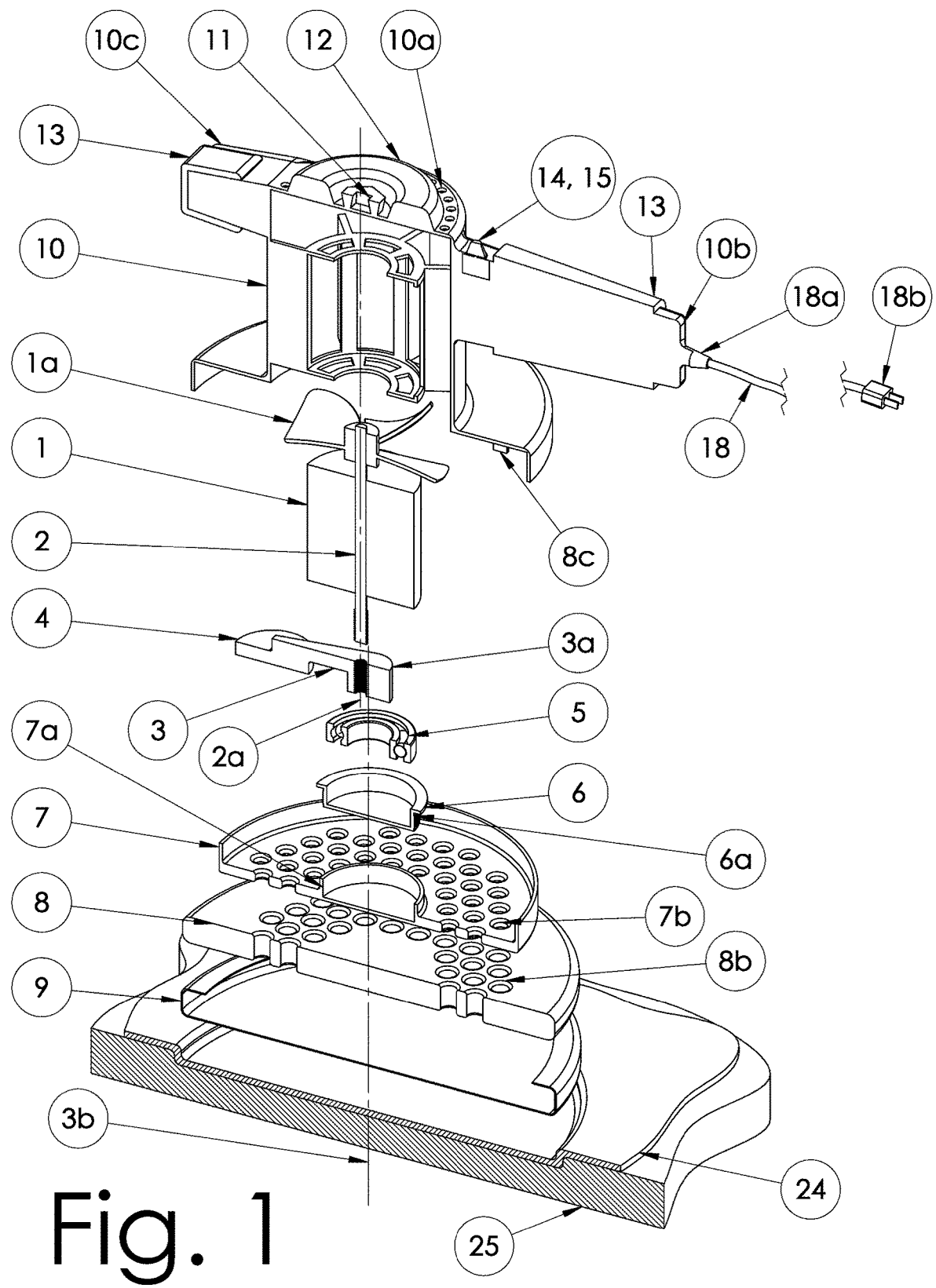
FIG. 1 is an exploded view of a motorized therapeutic massage device, according to one embodiment of the present disclosure.

Before explaining the disclosed embodiments of the present invention in detail it is to be understood that the invention is not limited in its application to the details of the particular arrangement shown since the invention is capable of other embodiments. Also, the terminology used herein is for the purpose of illustration and description and not of limitation.

An embodiment of the invention will reduce massage therapy treatment to a small number of sessions, possibly of less than a single hour each, providing a very recuperative and effective deep tissue massage to a patient.

According to an embodiment, a motorized massage device is provided with a contact surface arrangement having a low coefficient of friction. Previous motorized massage devices typically had an oscillating contact surface directly contacting a patient's skin where the contact surface included a composition of rigid plastic or terry cloth that can result in chafing, abrasion, or bruising of the massaged skin or tissue. Additionally, terry cloth or a similar pad cover is prone to disintegrate into airborne particles, which when breathed in, causes respiratory complications to the sinuses, throats and lungs in both the therapist and the patient.

According to an embodiment, a small, portable solution is provided as an alternative to using equipment that is difficult, if not impossible to transport to the user, or which may require the user to travel to the equipment. It is much more practical to employ the use of a small, portable solution in a users home, for example, than having the user travel to the massage therapy equipment to undertake numerous, less effective treatments.

One or more embodiments of the present invention provide an apparatus that improves over the prior art by:

providing a portable massage device that allows a user or a professional to treat himself or a patient in an office or at home;

providing a means for chiropractic physicians to relax his or her patients prior to providing adjustment(s);

providing a quickly detachable massage pad with a substantially smooth surface that minimizes the frictional engagement of the patients skin, and may be used thru a garment the patient is wearing over his skin, or upon bare skin;

providing a massage pad cover that when in use provides a further cooling effect to a contact surface arrangement of the massage device by drawing in cooling ambient air between the contact surface arrangement and the user's skin;

focusing on risks associated with chafing and burning of the skin, and with hair entanglement;

provide for a means to detect the pressure and temperature of the contact surface and display over limit pressure and temperature conditions;

providing a means to prevent objects such as hair and clothing from becoming entangled within the unit;

providing a means to bear down on a pressure pad disposed on the enclosure to achieve an even greater depth of massage, without causing pain or injury to the user or massage therapist;

providing a fan within the unit to cool the device and provide for a smaller, lighter, safer, more maneuverable and longer lasting product;

providing a means to attach accessories to the massage device to allow additional features and accessories to be used with the device; and providing additional safety features that are not found on existing products, so as to prevent injury to the users and damage to the apparatus. (hair and clothes entanglement, temp protection, rev limiter, pressure pad, grip pads, longer power cord, communication system).

Various embodiments of the present system improve over the prior art by:

providing a means to mount the device to and communicate with a computer controlled, 5 axis CNC (computer numerically controlled) motorized machine;

providing a means to input relative coordinate data from, and to capture topographical data of the individual being treated and communicate it to the CNC motorized machine;

providing a means for patient and therapist to verbally communicate in a high noise environment when a patient is receiving treatment; and providing a means to store and communicate data including, but not limited to position, pad pressure, temperature, rate of rotation, rate of travel, run time etc.

Definitions

The following terms, when used herein and capitalized or otherwise, are defined as follows:

"Contact Surface": See "Massage Pad":

"Massage Pad": Portion of the Device that couples the "Random orbital oscillating" motion, and the "Percussive" motion produced by the motor of the device, and their respective "Random orbital oscillating" and "Percussive" forces to human and animal skin and tissue. Even though it is understood that the "Massage Pad" does not physically contact either Skin or Tissue, as defined below, it is understood that the "Massage Pad Cover" does not inhibit any motion or forces, but acts to minimize the frictional engagement of the "Massage Pad" against the human or animal skin. As such, the "Massage Pad" and the "Massage Pad Cover" may be individually or collectively used interchangeably, or also be referred to as being part of the "Contact Element" or "Contact Surface Arrangement".

"Skin": Generally used to describe naked human skin. Also may include, but not be limited to the expanse of human skin, and the underlying "Tissue" disposed in proximity of the general area. Also may include the skin of animals, including but not limited to horses.

"Tissue": Generally used to describe human muscle tissue. Also may include, but not be limited to the skin, muscle fascia, tendons, cartilage, fat, blood vessels, lymphatic vessels, lymph nodes, internal organs, and animals.

"User": Generally used to describe a person operating the device. Also may include, but not be limited to a person using the machine on him or herself, or on another individual or an animal. Also may include, but not be limited to chiropractic physicians or massage, sports, or physical therapists, and a group or multiple groups of people. Also may include, but not be limited to one user receiving treatment from another individual, therapist, trainer, rehabilitation tech, or physician, where that user may be referred to as a "Patient".

"Muscle Spasm": Generally used to describe a sudden, involuntary contraction of a muscle, a group of muscles, or a similarly sudden contraction of an orifice. Also may include, but not be limited to a muscle cramp which is often accompanied by a sudden burst of pain, or involuntary muscle contractions, which may be more serious, depending on the cause. Also may include, but not be limited to insufficient hydration, muscle overload, and absence of electrolytes. Spasmodic muscle contraction may be due to a large number of medical conditions, including, but not limited to dystonias, or Hypertonic muscle spasms—a state of chronic, excessive tension in a resting muscle.

"Motor": Generally used to describe a motor powered by A/C, but may include, but not be limited to a DC motor, a reversible A/C or DC motor, a stepper motor, or any motor that is well understood by those of ordinary skill.

DESCRIPTION OF EXAMPLES

Various embodiments of the present disclosure relate to an apparatus for use in therapeutic massage applications in which forces are provided to an outer surface of the human body and subcutaneously within human tissues. The apparatus, according to one example, includes a covered, motor driven pad that imparts both random orbital and percussive forces to the skin and tissue of a human body in various contact arrangements between a massage pad and the skin and its underlying tissue.

Figure 2:
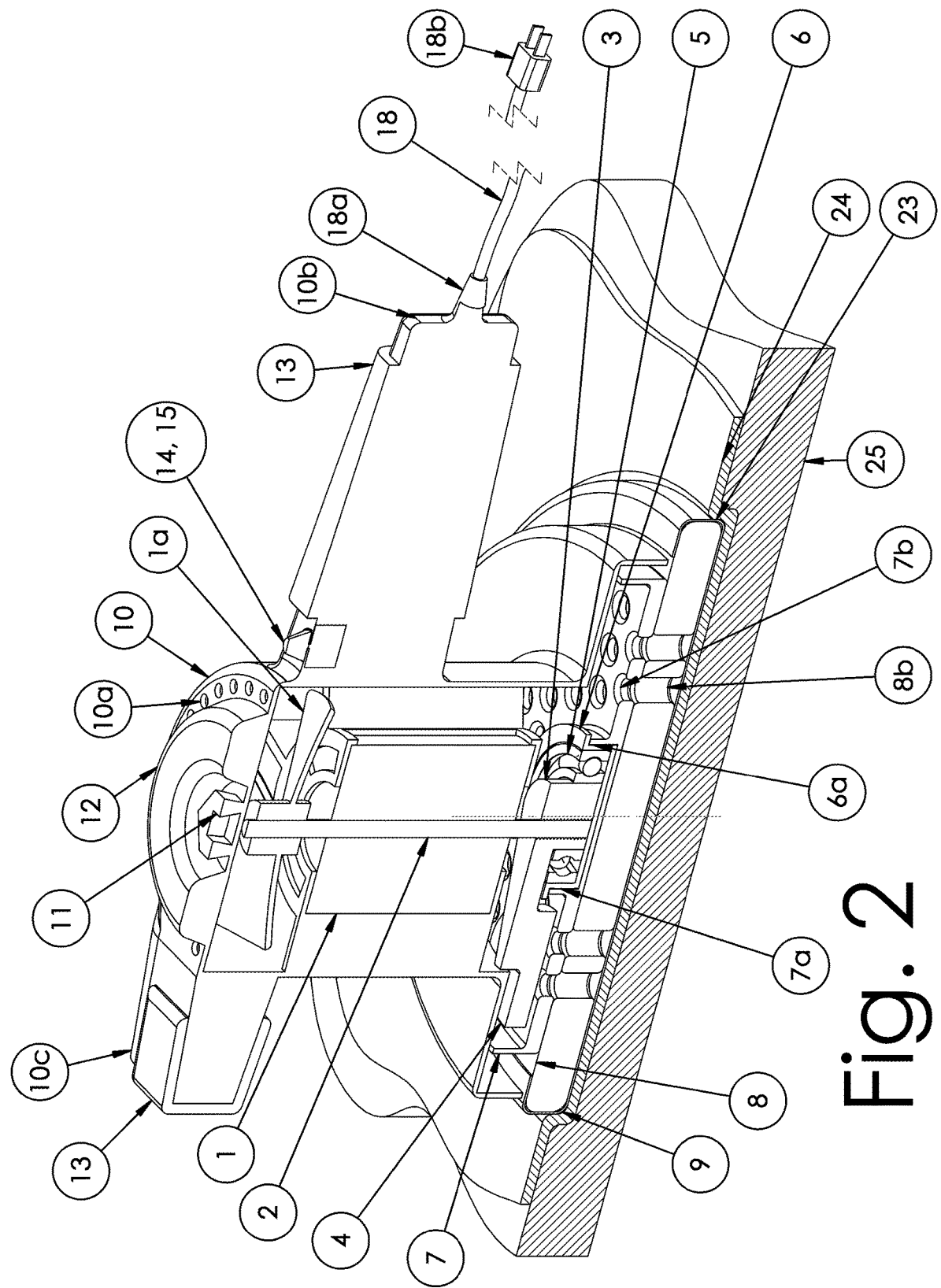
FIG. 2 is a cross sectional view of the motorized therapeutic massage device of FIG. 1.

Refer now to FIGS. 1 and 2, FIG. 1 shows an exploded view of one example embodiment of a portable, hand held, motorized therapeutic massage device and FIG. 2 shows a cross-section thereof. A motor 1 has a cooling fan 1a and a motor drive shaft 2 that delivers mechanical energy to a transfer member 3 having an offset hub 3a with center axis 3b. The transfer member 3 has a counter weight 4 and the offset hub 3a within an inner bearing race of a ball bearing assembly 5, also consisting of ball bearings and an outer bearing race which couple to quick disconnect mounting plate 6. A contact surface 8, 9, according to the present example, is coupled to the transfer member 3 by the offset hub 3a and has a center axis coincident with the center axis 3b of the offset hub 3a. The contact surface 8, 9, is coupled to the motor drive shaft 2 by means of the transfer member 3. The center axis 3b of the offset hub 3a and the center axis of the contact surface 8, 9 are offset from the center axis 2a of the motor drive shaft 2. The contact surface 8, 9, in the example, comprises a multilayered component including, but not limited to a layer of cellular foam or rubber, and a covering substantially including, but not limited to leather or woven cloth and vinyl. The quick disconnect mounting plate 6 has a quick disconnect part A 6a, that mates with quick disconnect part B 7a, disposed on a massage pad mounting plate (or rigid disk) 7. A plurality of sensors (not shown) in the motorized therapeutic massage device can measure at least one state of properties associated with the contact surface 8, 9, including, but not limited to temperature (see, for example, temperature sensor 8c in FIG. 1) or pressure (sensor not shown). According to certain embodiments, the plurality of sensors is coupled to an indicator or indicators in the motorized therapeutic massage device. A shutoff is configured to be activated when one or more of the plurality of sensors (for example, and not for limitation, a rotational motion sensor 16) exceeds a pre-set value.

According to this embodiment, the quick disconnect is shown as one example, and is not intended to limit other possible configurations, including, but not limited to reversing the motor 1, or having a lock, a detent, a turret or other style of chuck. A massage pad 8 is disposed adjacent to the massage pad mounting plate (or rigid disk) 7. The massage pad 8 may be composed of one or more materials, including but not limited to, cellular foam or rubber, expanded polyurethane, cellular rubber or a semi-rigid foam. Vent holes 7b and 8b provided in the massage pad mounting plate 7 and the massage pad 8 respectively, allow cool air to be pulled from the top of the unit through the enclosure air vents 10a by the cooling fan 1a to cool the motor 1, the massage pad 8 and the massage pad cover 9. Gripping the primary handle 10b and the secondary handle 10c, where in this example the secondary handle 10c has safety grip pads 13, the user can direct position the enclosure 10, so as to couple the force from the massage pad 8 thru the massage pad cover 9, the patients' garments (not shown), the patient's skin 24, and into the patient's muscle tissue 25. A pressure pad 12 disposed on the enclosure provides a means to bear down on to achieve an even greater depth of massage, without causing pain or injury to the user or massage therapist.

In a first arrangement, referring to FIGS. 1 and 2, for example, and not for limitation, the large surface area of the pad 8 parallel to the body of the patient is shown contacting the skin surface of the patient and providing shearing and stretching random orbital motion across the skin, while pressed into the patient's tissue with the large flat portion of the massage pad 8 and the massage pad cover 9 pressed into the muscle tissue 25. In this position, the flat portion of the massage pad 8 will impart a random orbital oscillating motion (i.e., the random orbital oscillating motion having a variable orbit diameter) to the skin 24 that it is in contact with, and the muscle tissue 25 that it is pressed into. Mainly friction force between the lateral pad surface and the skin surface at the contact area transfers lateral vibratory vibration from the pad 8 to the skin of the patient. With every rotation of the massage pad 8, shearing and stretching forces are coupled into the muscle tissue 25. In one example embodiment, the massage pad cover 9 is constructed of a flexible covering of one or more layers, and includes but is not limited to one or more materials such as leather, Teflon, woven cloth, or vinyl.

Continuing with the example, in a second arrangement, an edge surface (i.e., other than the large flat portion) of the pad 8 contacting the skin 24 provides deep pulsating vibrations into the skin surface typically at a normal or near normal axis with the skin surface.

Figure 3:
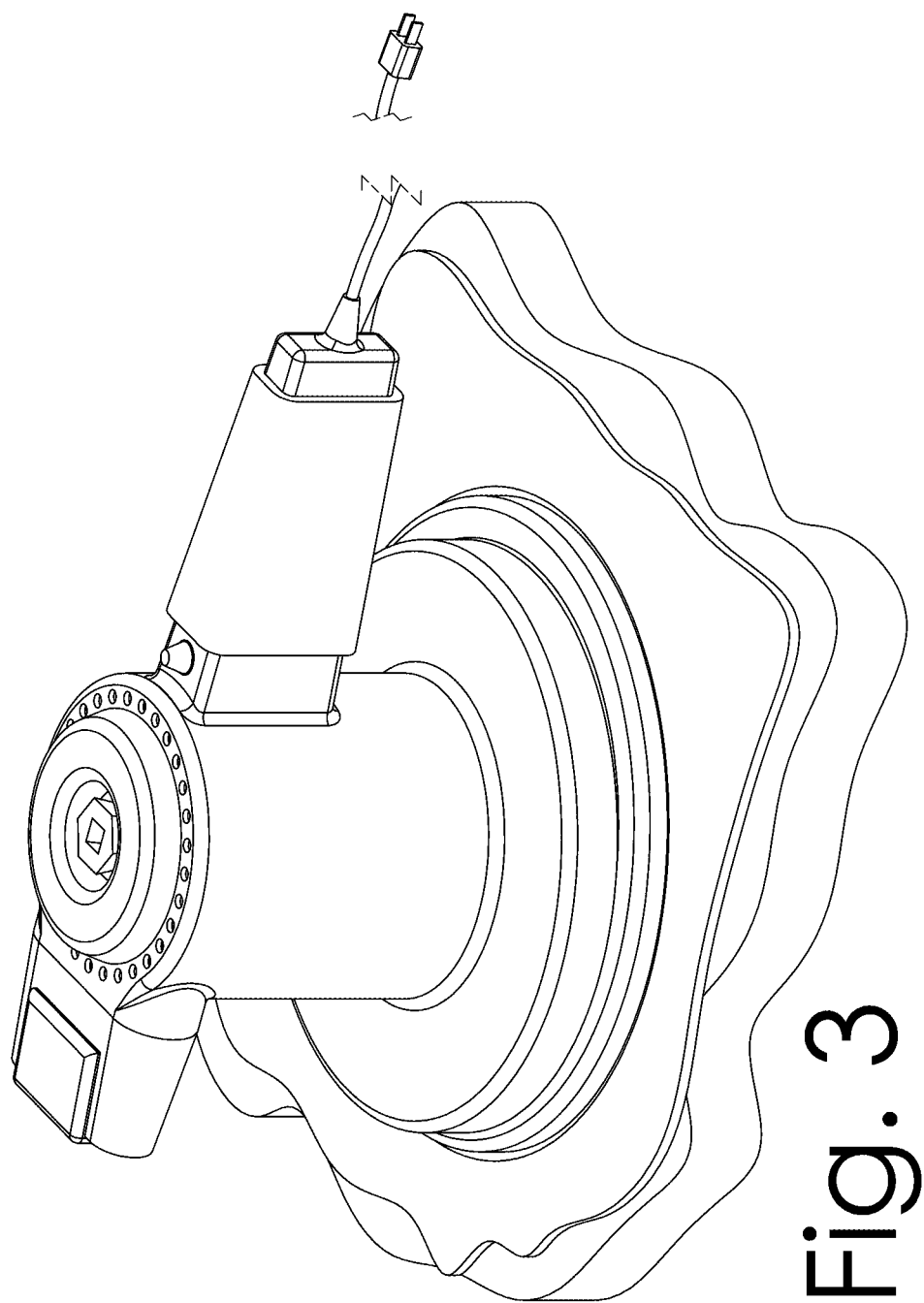
FIG. 3 is a perspective view of the motorized therapeutic massage device of FIG. 1.

With reference to FIGS. 1, 2, and 3, an exploded view, a cross-sectional view, and a perspective view, of an example embodiment of a motorized therapeutic massage device are shown, for example, and not for limitation, illustrating the mechanically engaged human skin and it's associated human tissue, created by the massage pad's cover when pressed into an expanse of the human skin and tissue.

Analysis using a stroboscopic light source has shown that this force propagates approximately 6 inches through the muscle tissue, and is visible as ripples in a wave. Because the human body is composed mostly of water, this should not be a surprise.

In physics, the phenomenon of resonant frequency will show that based on the density of the muscle tissue 25, there will be a preferred oscillating motion revolutions per minute (RPM) that will propagate a wave further than all other RPM's.

As an example, if a professional football player were suffering from a pulled thigh muscle, any exertion on the muscle would cause the muscle to contract into a muscle spasm. This is the body's self defense method, in which the thigh muscle is being contracted to prevent a more serious injury such as a muscle tear. The football player could loosen up the thigh muscle using a consumer version at his home, several times a day, largely by using the device in a random orbital oscillating force. The force on the muscle would cause delivery of compounds including but not limited to oxygen, blood and lymphatic fluids through the vessels and tissues, healing the injury and reducing swelling, and flushing toxins including but not limited to lactic acid out of the muscle tissue. This increased blood flow would further warm the area, causing vessels to stay dilated longer, thus helping the football player's body, in this example, to continue healing itself. As the muscle spasm eases, the player would be able to better tolerate a more aggressive percussive force, able to penetrate deeper into the tender muscle, and continued therapy thru a sports rehab trainer, to enable the player to play for a game that would otherwise not be able to play.

By promoting the circulation of substances in the body, many medical conditions can be improved. Patients having heart disease, diabetes, phlebitis, for example, and other illnesses resulting in compromised circulation of fluids including but not limited to blood and lymphatic fluid, and congestion within lungs and tissues would be benefited by the use of such therapy. The improvement of circulation would cause congested blood vessels and tissues to be flooded with oxygen, and waste products or toxins including but not limited to lactic acid to be flushed from the tissues and lymphatic vessels. An example of this would be forcing the blood from one's calves upwards towards the heart to prevent edema in the legs. The resulting reduction in swelling in the calves would allow increased flow of blood to continue to flush the calve muscles with blood, thereby opening up a pathway for the body to allow the circulation of blood and lymphatic fluids to continue to nourish and flush tissues that would otherwise fail to be nourished and flushed as effectively.

An embodiment of the disclosure is further related to massage devices used to reduce muscle spasms, by both warming up muscle tissues both prior to physical activity, and relaxing muscle tissues after physical activity. Muscle spasms that are so deep within large muscle tissues may be impossible to be treated using conventional massage therapy. The prior art discloses numerous massage devices and methods that have been used to treat muscles, muscle spasms, improve circulation, promote the flushing of waste products from tissues, and break up bronchial secretions, using massaging circular oscillations across the skin and tissue and alternatively percussive types of force directed generally normal to and into the skin and tissue.

Many prior art vibrators and massage devices require massage directly to the skin, and as such, are and are not effective for prolonged use, as chafing or burning of the skin can result. Many of these devices and treatments pose the risk of hair or clothes entanglement, and therefore require the patient not be clothed. Additionally, prior art devices are prone to overheating, forcing the user to wait between uses, to allow the device to cool down, or otherwise risk burning out the device, thereby requiring the device to be repaired or replaced. Frequently the prior art devices are mounted to a wall or disposed within a cart, making it difficult, if not impossible, to transport the device. For at least these reasons, many prior art devices require the patient to travel and come to be treated at a location where the treatment equipment is located.

Figure 4:
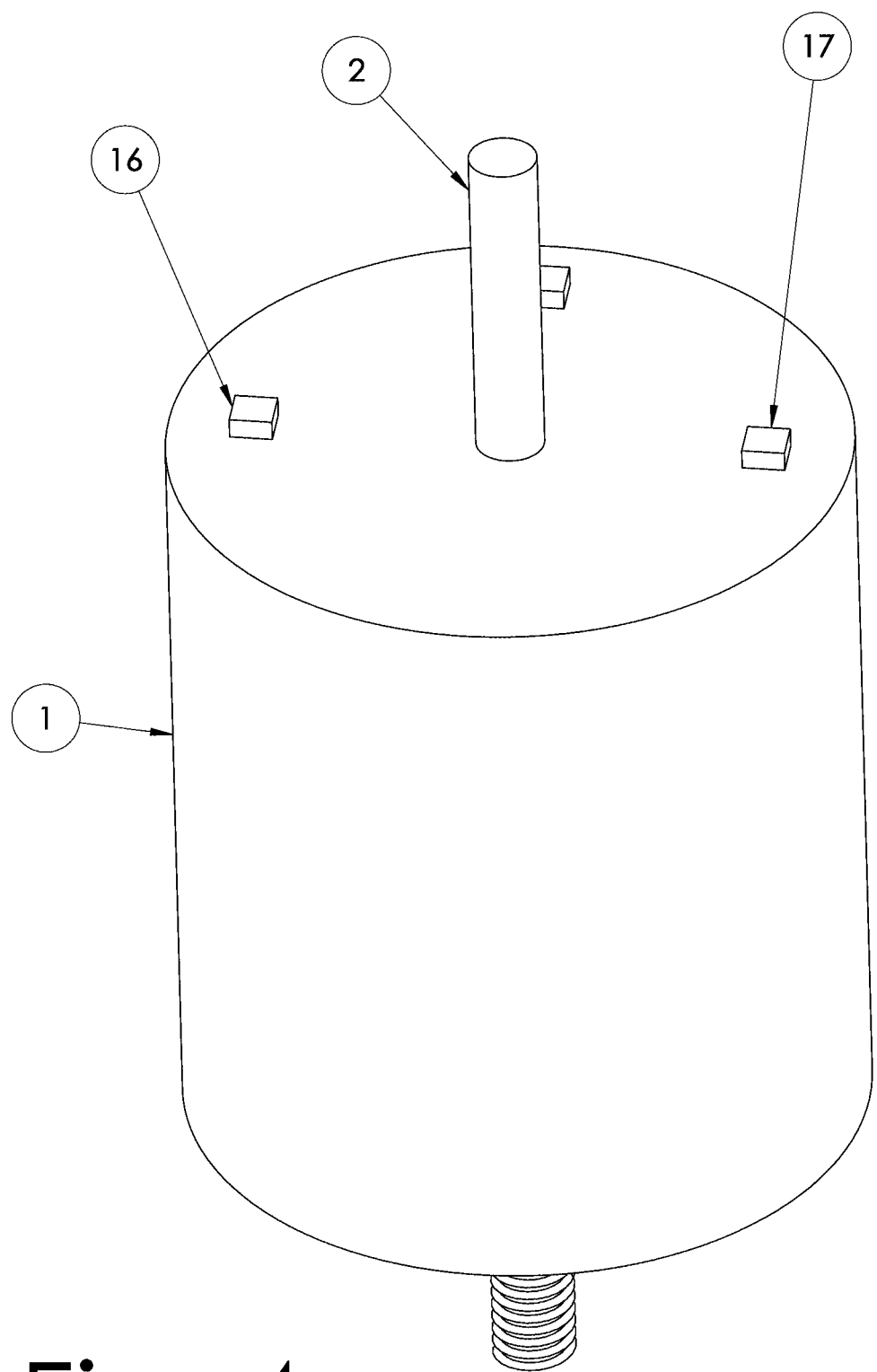
FIG. 4 is a perspective view of a motor in the motorized therapeutic massage device of FIG. 1.
Figure 5:
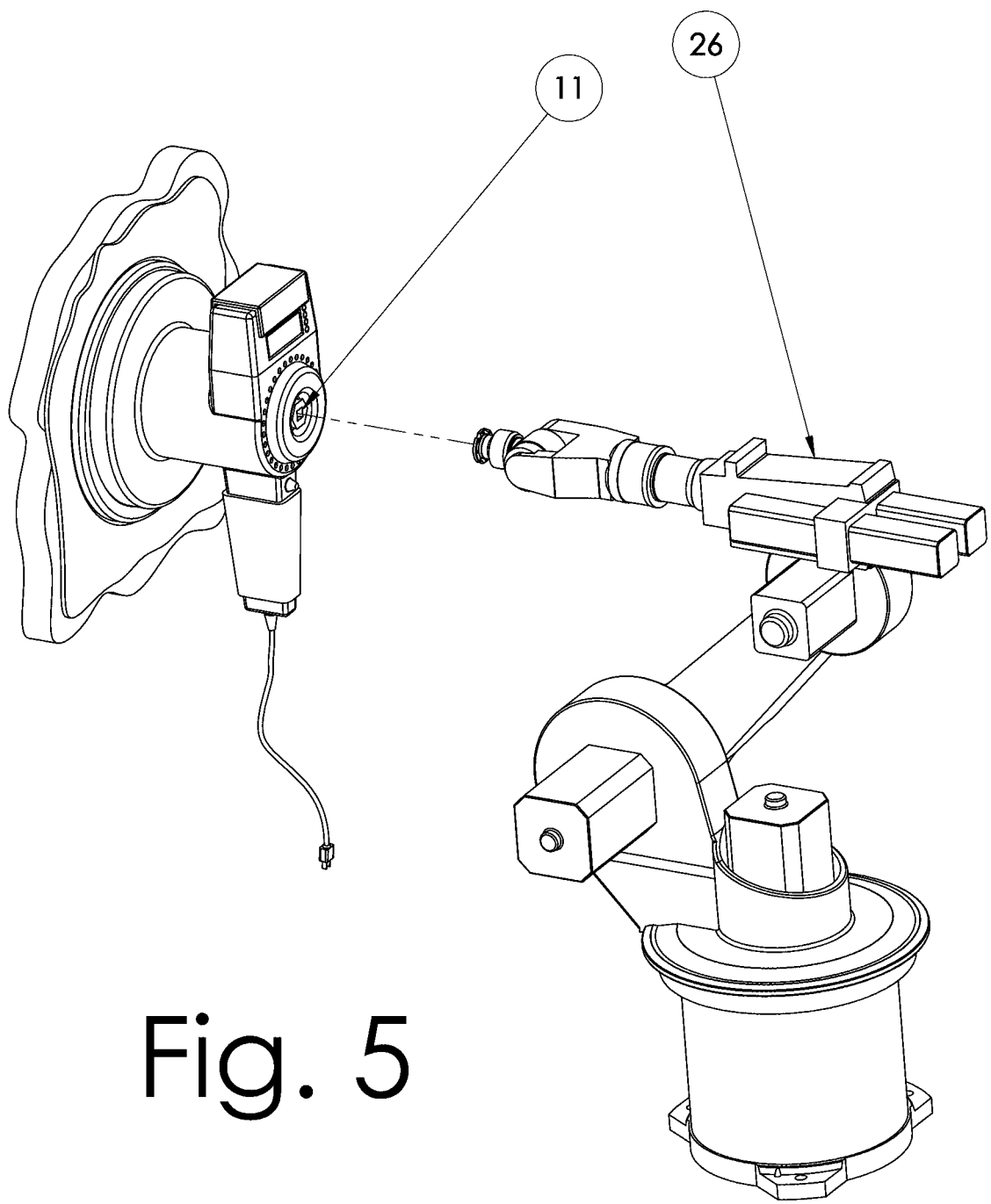
FIG. 5 is a perspective view of an accessory mount of the motorized therapeutic massage device of FIG. 1.

Referring again especially to FIG. 1, in the present example, AC power is provided to the motor 1 by a power cord 18, having both a plug 18b and a strain relief 18a. The AC power is switched by power switch 14 and the motor 1 is allowed to run at variable speeds by means of variable speed control 15, which in this embodiment, by example is incorporated into power switch 14, and includes, but is not limited to, a rheostat, a solid state controller, or a multi-position switch. Additionally, as shown in FIG. 4, other aspects may include but not be limited to high temperature protection 17 shutting off the motor 1 when monitored temperature indicates the motor 1 is overheating, or rev limiter 16 (e.g., with rotational motion sensor), preventing excessive RPM of the massage pad 8, should the operator lift the contact surface away from a patient's body part being treated. An embodiment of the device can provide a means to cool the massage pad 8 by any one or more, but not limited to, the vent holes 7b and 8b and arrangement that has already been discussed above, a Peltier solid state cooling chip, or a secondary Fan, or the like.

FIGS. 1, 2, 3, and 53 show accessory mount 11, which allows accessories to be attached to the unit for other purposes, or the unit to be attached for other purposes, including, but not limited to mounting to a massage chair, a wall mount, or on a robotically controlled system 26.

Another embodiment includes a mobile service including but not limited to a massage therapist coming on site to provide massage services at various venues, including workplaces or conventions, performing massage services on attendees positioned on both massage chairs and massage tables.

Other embodiments include attachment of the device to a 5-axis robotically controlled system 26, having an emergency stop switch (not shown), which is well known in the manufacturing industry, and is routinely used for computer numerically controlled (CNC) milling processes, using 3-dimensional space, as defined by the Cartesian coordinate system. This aspect includes, but is not limited to a computer controlled robotic arm, a combination of gantry arms, or the like, attached to the massage device discussed above. An example embodiment of such a system stores patient profiles that for each patient can include, but is not limited to, account information, medical records, body topography, preferences for programmed default and personalized massage paths, RPM speeds, rate of travel (feeds), contact surface pressure, angles of tilt and rotation, and exclusion areas.

Such an embodiment may include either manually mapping the topography of the patient, using methods including but not be limited to capturing spatial data points moving the massage pad over the body, by means of a joystick controller to mapping the topography of the patient using a laser scanner. Additionally, audio and video data can be captured when a patient is receiving treatment. Another aspect may include, but not be limited to, a plurality of massage centers located in airports or other locations connected via a computer network that could provide the patient at any of the locations with individualized massage therapy program. This would allow weary travelers to receive their desperately needed massage just the way they like it, no matter where in the world they are.

Like the mobile service described above, one or more robotically controlled systems 26 could be disposed within a mobile vehicle, including but not limited to a van, a mobile home, a recreational vehicle, or travel trailer. One such embodiment includes, but is not limited to: sporting events, concerts, special events, and corporate events. Patient profiles would be accessed via wireless cellular networks.

One embodiment of such a system can include, but is not limited to, a web based scheduling system that allows the user to find locations, schedule appointments for both manual and robotic massage sessions, and pay via the user's smart phone.

One should note that the above described various example embodiments of the invention, are for illustration purposes only, and are not for the purpose of limiting of its scope. The various examples teach various changes in form, details, improvements and other embodiments that may be equally effective. Such improvements are intended to be part of this disclosure without departing from the scope of the invention as defined by the appended claims.

Non-limiting Examples

Flowchart and block diagrams that may be shown in the Figures and/or described herein illustrate the architecture, functionality, and operation of possible implementations of systems, devices, and methods, according to various embodiments of the present invention. In this regard, each block in a flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although the present specification may describe components and functions implemented in the embodiments with reference to particular standards and protocols, the disclosure is not limited to such standards and protocols. Each of the standards represent examples of the state of the art. Such standards are from time-to-time superseded by faster or more efficient equivalents having essentially the same functions.

The illustrations of examples described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Although specific embodiments have been illustrated and described herein, it should be appreciated that any arrangement calculated to achieve the same purpose may be substituted for the specific embodiments shown. The examples herein are intended to cover any and all adaptations or variations of various embodiments. Combinations of the above embodiments, and other embodiments not specifically described herein, are contemplated herein.

The Abstract is provided with the understanding that it is not intended be used to interpret or limit the scope or meaning of the claims. In addition, in the foregoing Detailed Description, various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. The term "another", as used herein, is defined as at least a second or more. The terms "including" and "having," as used herein, are defined as comprising (i.e., open language). The term "coupled," as used herein, is defined as "connected," although not necessarily directly, and not necessarily mechanically. "Communicatively coupled" refers to coupling of components such that these components are able to communicate with one another through, for example, wired, wireless or other communications media. The term "communicatively coupled" or "communicatively coupling" includes, but is not limited to, communicating electronic control signals by which one element may direct or control another. The term "configured to" describes hardware, software or a combination of hardware and software that is adapted to, set up, arranged, built, composed, constructed, designed or that has any combination of these characteristics to carry out a given function. The term "adapted to" describes hardware, software or a combination of hardware and software that is capable of, able to accommodate, to make, or that is suitable to carry out a given function.

The corresponding structures, materials, acts, and equivalents of all means or step plus function elements in the claims below are intended to include any structure, material, or act for performing the function in combination with other claimed elements as specifically claimed. The description herein has been presented for purposes of illustration and description, but is not intended to be exhaustive or limited to the examples in the form disclosed. Many modifications and variations will be apparent to those of ordinary skill in the art without departing from the scope of the examples presented or claimed. The disclosed embodiments were chosen and described in order to explain the principles of the embodiments and the practical application, and to enable others of ordinary skill in the art to understand the various embodiments with various modifications as are suited to the particular use contemplated. It is intended that the appended claims below cover any and all such applications, modifications, and variations within the scope of the embodiments.

What is claimed is:

1. A motorized therapeutic massage device comprising:
   a computer-controlled electrical motor having a motor drive shaft that is rotationally driven by the computer-controlled electrical motor;

a contact surface arrangement having an outer surface for contacting a body of a user to be treated with therapeutic massage, the contact surface arrangement being coupled to the motor drive shaft by means of a rigid transfer member having an offset hub, offset from a center axis of rotation of the motor drive shaft, the offset hub being directly coupled and rotationally coupled to a bearing assembly and thereby rotationally coupled to the contact surface arrangement, a center axis of the motor drive shaft at the offset hub being offset from a center axis of the offset hub which is coincident to a center axis of the contact surface arrangement, and wherein the motor drive shaft is coupled to the outer surface of the contact surface arrangement to thereby rotationally drive and impart rotational motion to the outer surface of the contact surface arrangement;

a rotational motion sensor for sensing rotational motion of the outer surface; and a computer controller, communicatively coupled with the computer-controlled electrical motor and the rotational motion sensor, the computer controller, responsive to executing computer instructions, being adapted to perform the following operations:

determining a first configured pre-set value for rotational motion revolutions per minute (RPM) for the outer surface of the contact surface arrangement individualized to the user for treating the user's body with the therapeutic massage; and controlling, with the computer controller, the computer-controlled electrical motor to impart a rotational motion to the outer surface, based on a rotational motion sensed by the rotational motion sensor, being imparted to the outer surface and the first configured pre-set value individualized to the user.

2. The motorized therapeutic massage device of claim 1, further comprising a pressure sensor for sensing a pressure exerted by the outer surface of the contact surface arrangement on the body of the user, and wherein the computer controller is communicatively coupled with the pressure sensor, and the computer controller responsive to executing computer instructions, being adapted to perform the following operations:

controlling the computer-controlled electrical motor, based on the pressure, sensed by the pressure sensor, that is exerted by the outer surface of the contact surface arrangement on the body of the user.

3. The motorized therapeutic massage device of claim 1, comprising a limiter and/or a shutoff configured to be activated to limit and/or stop rotational motion of the outer surface of the contact surface arrangement in response to one or more of the following:

one or more sensors of the motorized therapeutic massage device exceed above respective one or more configured pre-set values; or one or more sensors of the motorized therapeutic massage device exceed below respective one or more configured pre-set values.

4. The motorized therapeutic massage device of claim 1, wherein the contact surface arrangement comprises a multilayered component arrangement comprising a massage pad and a massage pad cover that covers the massage pad and provides the outer surface of the contact surface arrangement for contacting the user's body to be treated with therapeutic massage, the massage pad including a set of vent holes through the massage pad, the set of vent holes rotationally move with the rotationally moving massage pad and pull air to cool the massage pad and the massage pad cover to cool the outer surface of the contact surface arrangement.

5. The motorized therapeutic massage device of claim 4, wherein the massage pad cover, while in use with the rotationally moving massage pad, provides a further cooling effect to the contact surface arrangement by drawing in cooling ambient air between the contact surface arrangement and the user's skin.

6. The motorized therapeutic massage device of claim 4, wherein the massage pad cover is constructed of a flexible covering material and comprises at least one of
  leather,
  woven cloth, or
  woven cloth and vinyl.

7. The motorized therapeutic massage device of claim 6, wherein the massage pad cover is constructed of the flexible covering material and is removable from the massage pad by the user.

8. The motorized therapeutic massage device of claim 1, wherein the contact surface arrangement comprises a multilayered component arrangement comprising a massage pad and a massage pad cover that covers the massage pad and provides the outer surface of the contact surface arrangement for contacting the user's body to be treated with the therapeutic massage, the massage pad comprises at least one of
  cellular foam,
  cellular rubber,
  expanded polyurethane, or
  semi-rigid foam.

9. The motorized therapeutic massage device of claim 1, further comprising a pressure sensor for sensing a pressure associated with the contact surface arrangement, and wherein the computer controller, responsive to executing computer instructions, being adapted to perform the following operations:

maintaining the rotational motion of the outer surface of the contact surface arrangement at the configured pre-set value for rotational motion revolutions per minute (RPM) individualized to the user for treating the user's body with the therapeutic massage, while the pressure sensor senses a pressure that does not exceed a configured pre-set value.

10. The motorized therapeutic massage device of claim 1, wherein the computer controller, responsive to executing computer instructions, being adapted to perform the following operations:

maintaining the rotational motion of the outer surface of the contact surface arrangement at the configured pre-set value for imparting rotational motion, by the motor drive shaft, to the outer surface of the contact surface arrangement to thereby treat the user's body with therapeutic massage at a particular oscillating motion revolutions per minute (RPM), individualized to the user, that propagates from the contact surface arrangement a massage force wave suitable for penetrating through the user's muscle tissue further than any other massage force waves resulting from other rotational motion RPM's imparted to the outer surface of the contact surface arrangement, other than the particular oscillating motion RPM individualized to the user.

11. The motorized therapeutic massage device of claim 1, wherein the computer controller, responsive to executing computer instructions, being adapted to perform the following operations:

limit or shutoff the computer-controlled electrical motor in response to one or more of the following:

one or more sensors of the motorized therapeutic massage device exceed above respective one or more configured pre-set values; or one or more sensors of the motorized therapeutic massage device exceed below respective one or more configured pre-set values.

12. The motorized therapeutic massage device of claim 1, in which the motorized therapeutic massage device includes an accessory mount and thereby is communicatively coupled to and disposed upon a robotically controlled system to provide a full body massage to the user by the robotically controlled system moving and controlling the motorized therapeutic massage device on the user's body and having the ability by such movement and control to tilt, rotate, and move the motorized therapeutic massage device thru space in three spatial dimensions, the accessory mount coupling between the motorized therapeutic massage device and the robotically controlled system, one or more of the following:

data signals;

control signals; or electrical power signals.

13. A motorized therapeutic massage device comprising:
   a computer-controlled electrical motor having a motor drive shaft that is rotationally driven by the computer-controlled electrical motor;
   a contact surface arrangement being coupled to the motor drive shaft by means of a rigid transfer member having an offset hub, offset from a center axis of rotation of the motor drive shaft, the offset hub being directly coupled and rotationally coupled to a bearing assembly and thereby rotationally coupled to the contact surface arrangement to rotationally drive and impart rotational motion to the contact surface arrangement and thereby treat a body of a user with therapeutic massage;
   an accessory mount structure mechanically coupled to an outer surface of a housing of the motorized therapeutic massage device, the accessory mount structure including an attachment structure that is user mountable with, and user attachable to, a mechanically compatible attachment structure on a support structure thereby attaching the motorized therapeutic massage device to the support structure that supports the motorized therapeutic massage device while treating the body of the user with the therapeutic massage;
     a computer controller, communicatively coupled with the computer-controlled electrical motor, the computer controller, responsive to executing computer instructions, being adapted to control the computer-controlled electrical motor to impart rotational motion to the contact surface arrangement to treating the body of the user with the therapeutic massage.

14. The motorized therapeutic massage device of claim 13, wherein the support structure comprises at least one of a massage chair, a wall mount, or a robotically controlled system, thereby supporting the motorized therapeutic massage device while treating the body of the user with the therapeutic massage.

15. A therapeutic massage device communication system comprising:
   a plurality of therapeutic massage devices that are separate from each other, each of a first therapeutic massage device and a second therapeutic massage device, in the plurality, being configured to a device configuration selected from the following:
     a manually operated motorized therapeutic massage device, or
     a motorized therapeutic massage device communicatively coupled to and disposed upon a robotically controlled system; and wherein
   each of the first therapeutic massage device and the second therapeutic massage device comprising:
     a computer-controlled electrical motor having a motor drive shaft that is rotationally driven by the computer-controlled electrical motor;
     a contact surface arrangement being coupled to the motor drive shaft by means of a rigid transfer member having an offset hub, offset from a center axis of rotation of the motor drive shaft, the offset hub being coupled to the contact surface arrangement, and wherein the motor drive shaft is coupled to the contact surface arrangement to rotationally drive and impart rotational motion to the contact surface arrangement and thereby treat a body of a user with therapeutic massage;
     at least one sensor including a rotational motion sensor for sensing rotational motion of the contact surface arrangement; and
     a computer controller, communicatively coupled with the computer-controlled electrical motor, the at least one sensor, and a computer network; and wherein
   the computer controller, responsive to executing computer instructions, being adapted to perform the following operations:
     determining a configured pre-set value for rotational motion revolutions per minute (RPM) for the contact surface arrangement individualized to the user for treating the user's body with a same therapeutic massage by either the first therapeutic massage device or the second therapeutic massage device, wherein the determining the configured pre-set value being performed by the computer controller by at least one of:
       accessing data stored in the respective each therapeutic massage device, the data corresponding to the configured pre-set value; or
       accessing data corresponding to the configured pre-set value by network communication with a computer system communicatively coupled to the computer network;
     controlling, with the computer controller, the computer-controlled electrical motor, to rotationally impart rotational motion to the contact surface arrangement based on the configured pre-set value for rotational motion revolutions per minute (RPM); and
     communicating, with the computer controller, data corresponding to sensor data from the at least one sensor, over the computer network, to the computer system communicatively coupled to the computer network, wherein the computer system includes one or more of: a robotically controlled system, a computer, a smart phone, or another of the first therapeutic massage device or the second therapeutic massage device.

16. The therapeutic massage device communication system of claim 15, wherein the computer controller of each of the first therapeutic massage device and the second therapeutic massage device, responsive to executing computer instructions, being adapted to perform the following operations:
   maintaining a rotational motion of the respective contact surface arrangement, in each of the first therapeutic massage device and the second therapeutic massage device, at the configured pre-set value for imparting rotational motion RPM to the respective contact surface arrangement to thereby treat the user's body with the therapeutic massage individualized to the user for penetrating through the user's muscle tissue.

17. The therapeutic massage device communication system of claim 15, further comprising a web based scheduling system that allows the user to find locations of one or more of the plurality of therapeutic massage devices, to schedule appointments for either manual or robotic massage sessions with the one or more of the plurality of therapeutic massage devices, and to pay via the user's smart phone.

18. The therapeutic massage device communication system of claim 15, wherein the first therapeutic massage device is located remote from the computer system and the computer controller of the first therapeutic massage device, responsive to executing computer instructions, being adapted to communicate data signals to, and receive data signals and control signals from, a second computer system by communication over the computer network.

19. The therapeutic massage device communication system of claim 15, wherein the first therapeutic massage device is a motorized therapeutic massage device communicatively coupled to and disposed upon a robotically controlled system remotely located from the second therapeutic massage device.

20. The therapeutic massage device communication system of claim 15, wherein the first therapeutic massage device is a motorized therapeutic massage device including an accessory mount and thereby is communicatively coupled to and disposed upon a robotically controlled system to provide a full body massage to the user by the robotically controlled system moving and controlling the motorized therapeutic massage device on the user's body and having the ability by such movement and control to tilt, rotate, and move the motorized therapeutic massage device thru space in three spatial dimensions, the accessory mount coupling between the motorized therapeutic massage device and the robotically controlled system, one or more of the following:
  data signals;
  control signals; or
  electrical power signals.

* * * * *